(12) United States Patent
Dickinson et al.

(10) Patent No.: US 8,883,726 B2
(45) Date of Patent: *Nov. 11, 2014

(54) FIBROBLAST GROWTH FACTOR 21 VARIANTS

(71) Applicant: Eli Lilly and Company, Indianapolis, IN (US)

(72) Inventors: Craig Duane Dickinson, San Diego, CA (US); David Albert Driver, Solana Beach, CA (US); Ryan James Darling, Fishers, IN (US); Malgorzata Donata Gonciarz, Indianapolis, IN (US); Radmila Micanovic, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/965,243

(22) Filed: Aug. 13, 2013

(65) Prior Publication Data

US 2013/0324460 A1  Dec. 5, 2013

Related U.S. Application Data

(63) Continuation of application No. 13/626,308, filed on Sep. 25, 2012, now Pat. No. 8,541,369.

(60) Provisional application No. 61/542,906, filed on Oct. 4, 2011.

(51) Int. Cl.
*A61K 38/18* (2006.01)
*C07K 14/50* (2006.01)
*A61K 38/00* (2006.01)

(52) U.S. Cl.
CPC .............. *C07K 14/50* (2013.01); *A61K 38/00* (2013.01)
USPC ........................................... 514/9.1; 530/399

(58) Field of Classification Search
None
See application file for complete search history.

(56) References Cited

U.S. PATENT DOCUMENTS

2012/0177646 A1  7/2012  Belouski et al.

FOREIGN PATENT DOCUMENTS

| EP | 1218509 | 4/2009 |
|---|---|---|
| EP | 2189475 | 5/2010 |
| WO | 03011213 | 2/2003 |
| WO | 2005061712 | 7/2005 |
| WO | 2006028595 | 3/2006 |
| WO | 2006028714 | 3/2006 |
| WO | 2008121563 | 10/2008 |
| WO | 2009149171 | 12/2009 |
| WO | 2010065439 | 6/2010 |
| WO | 2010129503 | 11/2010 |
| WO | 2010129600 | 11/2010 |

OTHER PUBLICATIONS

Berglund, Eric D., et al., Fibroblast Growth Factor 21 Controls Glycemia Via Regulation of Hepatic Glucose Flux and Insulin Sensitivity, Endocrinology, Sep. 2009, 150 (9), pp. 4084-4093.
Kharitonenkov, Alexei, et al., FGF-21 as a Novel Metabolic Regulator, J. Clin. Invest., 2005, 115 (6), pp. 1627-1635.
Kharitonenkov, Alexei, et al., The Metabolic State of Diabetic Monkeys is Regulated by Fibroblast Growth Factor-21, Endocrinology, 2007, 148 (2), pp. 774-781.
Kharitonenkov, Alexei, et al., Fibroblast Growth Factor-21 as a Therapeutic Agent for Metabolic Diseases, Biodrugs, 2008, 22 (1), pp. 37-44.
Micanovic, Radmila, et al., Different Roles of N- and C-Termini in the Functional Activity of FGF21, J. Cell. Physiol. 2009, 219: pp. 227-234.
Wente, Wolf, et al., Fibroblast Growth Factor-21 Improves Pancreatic β-Cell Function and Survival by Activation of Extracellular Signal-Reglated Kinase ½ and Akt Signaling Pathways, Diabetes, 2006, 55, pp. 2470-2478.
Wu, Xinle, et al., C-Terminal Tail of FGF19 Determines Its Specificity Toward Klotho Co-Receptors, J. Biol. Chem., Nov. 28, 2008, vol. 283, No. 48, pp. 33304-33309.
Yie, Junming, et al., FGF21 N- and C-Termini Play Different Roles in Receptor Interaction and Activation, FEBS Letters, 2009, 583 pp. 19-24.

*Primary Examiner* — Christine J Saoud
(74) *Attorney, Agent, or Firm* — Matthew T. Lord; Robert B. Johnson

(57) ABSTRACT

This present invention relates to pharmacologically potent and/or stable variants of human fibroblast growth factor 21 (FGF21), pharmaceutical compositions comprising FGF21 variants, and methods for treating type 2 diabetes, obesity, dyslipidemia, or metabolic syndrome, or any combination thereof, using such variants.

6 Claims, No Drawings

FIBROBLAST GROWTH FACTOR 21 VARIANTS

This present invention relates to variants of human fibroblast growth factor 21 (FGF21), pharmaceutical compositions comprising FGF21 variants, and methods for treating type 2 diabetes, obesity, dyslipidemia, or metabolic syndrome, or any combinations thereof.

FGF21 is a hormone that functions as an important metabolic regulator of glucose and lipid homeostasis. FGF21 promotes glucose uptake in adipocytes by up-regulating GLUT1 expression, a mechanism distinct from that of insulin. In diabetic rodents and monkeys, human FGF21 lowered fasting serum concentrations of glucose, and reduced fasting serum concentrations of triglycerides, insulin and glucagon. Furthermore, in rodent models of diet induced obesity, FGF21 administration led to cumulative body weight loss in a dose dependent manner. Thus, FGF21 has potential utility for the treatment of diabetes, obesity, dyslipidemia, and metabolic syndrome.

Variants of human FGF21 have been described in WO2010/065439, WO2006/028595, and WO2005/061712.

Problems associated with human wild type FGF21 and known variants of human FGF21 are the low pharmacological potency and/or pharmaceutical stability of the molecules. Thus, there is still a need for alternative FGF21 variants that are potent and/or stable.

The present invention provides alternative variants of human FGF21 having advantages over human wild type FGF21 and known variants of human FGF21 disclosed in the art. These advantages include improved pharmacological potency and/or improved pharmaceutical stability. Certain FGF21 variants of the present invention have one or more advantageous physiochemical characteristics that are useful for efficient manufacturing and/or formulation as a therapeutic protein, including reduced proteolytic degradation in vivo, reduced susceptibility to oxidation, lowered propensity to aggregate at high concentrations, lowered levels of post-translational modifications during production in mammalian cell systems, increased compatibility with certain preservatives, and/or improved chemical stability. Additionally, the FGF21 variants of the present invention are potentially useful for the treatment of type 2 diabetes, obesity, dyslipidemia, or metabolic syndrome or any combination thereof.

The present invention provides a variant of human fibroblast growth factor 21 (FGF21), wherein the amino acid sequence is (SEQ ID NO: 13)
HPIPDSSPLLQFGGQVRQRYLYTDDAQQTECHLEIREDGTVGCAADQS

PESLLQLKALKPGVIQILGVKTSRFLCQRPDGALYGSLHFDPEACSFR

EX$_1$LLEDGYNVYQSEAHGLX$_2$LHLPGDKSPHRKPAPRGPARFLPLPGLP

PALPEPPGILAPQPPDVGSSDPX$_3$X$_4$LVX$_5$PSQLLSPSFLG wherein X$_1$ is L or D, X$_2$ is P or W, X$_3$ is L or Y, X$_4$ is S or R, and X$_5$ is G or E.

The present invention provides a variant of human fibroblast growth factor 21 (FGF21), wherein the amino acid sequence is (SEQ ID NO: 1)
HPIPDSSPLLQFGGQVRQRYLYTDDAQQTECHLEIREDGTVGCAADQS

PESLLQLKALKPGVIQILGVKTSRFLCQRPDGALYGSLHFDPEACSFR

EDLLEDGYNVYQSEAHGLPLHLPGDKSPHRKPAPRGPARFLPLPGLPP

ALPEPPGILAPQPPDVGSSDPLRLVEPSQLLSPSFLG.

The present invention also provides a pharmaceutical composition comprising a variant of human FGF21 of the present invention, as described herein, and at least one pharmaceutically acceptable carrier, diluent, or excipient, and optionally other therapeutic ingredients.

The present invention also provides a method of treating type 2 diabetes, obesity, dyslipidemia, or metabolic syndrome, or any combination thereof, in a patient comprising administering to the patient a variant of human FGF21 of the present invention, as described herein.

The present invention also provides a method of treating type 2 diabetes, obesity, dyslipidemia, or metabolic syndrome, or any combination thereof, in a patient comprising administering to the patient a pharmaceutical composition of the present invention, as described herein.

Furthermore, the present invention provides a variant of human FGF21 of the present invention, as described herein, for use in therapy. Preferably, the present invention provides a variant of human FGF21 of the present invention, as described herein, for use in the treatment of type 2 diabetes, obesity, dyslipidemia, or metabolic syndrome, or any combination thereof.

Furthermore, the present invention provides the use of a variant of human FGF21 of the present invention, as described herein, in the manufacture of a medicament for the treatment of type 2 diabetes, obesity, dyslipidemia, or metabolic syndrome, or any combination thereof.

Full length human wild type FGF21 is a 208 amino acid polypeptide containing a 27 amino acid signal peptide. Mature human wild type FGF21 comprises the full length polypeptide without the 27 amino acid signal peptide, resulting in a 181 amino acid polypeptide (SEQ ID NO:2). The changes in amino acid positions of the FGF21 variants of the present invention are determined from the amino acid positions in the polypeptide of mature human wild type FGF21 (SEQ ID NO:2). Thus, a substitution described herein as "A31C" refers to substitution of the amino acid Cys for the wild type amino acid Ala at position 31 of the mature human wild type FGF21 protein.

It is important to note that a substitution of one amino acid residue in a particular variant may affect the characteristics of the variants as a whole, and that overall effect may be beneficial or detrimental to the pharmacological potency and/or pharmaceutical stability. For example, one amino acid substitution, P115W, increases the potency of the FGF21 variant, however P115W is also believed to contribute to the self-interactions that cause aggregation (see Example 5). Therefore, the overall effect is detrimental to the variants, and thus the substitution P115W is not included in the preferred FGF21 variants of the present invention.

Certain variants of human FGF21 of the present invention are potent, biologically active proteins as demonstrated for SEQ ID NO:1 in Examples 2 and 3. The preferred FGF21 variants of the present invention contain amino acid substitutions that together not only improve pharmacological potency, but also are compatible with other amino acid changes that, in turn, provide for improved physiochemical properties and increased in vivo stability. The group of amino acid substitutions in the preferred FGF21 variants of the present invention that improve potency include D127K, S167R, G174L, R175L, and A180L (see Examples 2 and 3).

Exposure of a concentrated protein solution of human wild type FGF21 to a pharmaceutical preservative, such as m-cresol, increases the propensity of the protein to form aggregates. Structural stabilization through the introduction of an additional disulfide bond improves the preservative compatibility as well as the thermal stability of human wild type FGF21. The FGF21 variants of the present invention incorporate the amino acid substitutions A31C and G43C that greatly improve thermal stability and preservative compatibility without compromising biological activity. High potency variants of FGF21 that also include the A31C/G43C substitutions have been described previously. Those reported variants display significantly improved preservative compatibility relative to wild type FGF21, but they are still prone to aggregation. Aggregation is known to increase the risk of immunogenicity, thereby reducing the acceptability of the variants as a therapeutic protein.

To minimize this detrimental aggregation, preferred variants of the present invention include the amino acid substitution L98D, which results in a significantly lower high molecular weight aggregate formation at high concentrations (see Example 5). Advantageously, the amino acid substitution L98D does not decrease the potency of the variants.

A preferred commercial expression system for manufacture of the FGF21 variants of the present invention is the mammalian CHO-K1 cell line. However, the mammalian cell lines CHO-K1 and HEK293 may cause post-translational modifications to mature human wild type FGF21 through sulfation of the tyrosine side chain at position 179. Sulfation of tyrosine residues at positions 179 and 180 (if present) decreases potency and is an undesirable source of product heterogeneity. Thus, when an FGF21 protein having Tyr at position 179 and/or 180 is expressed from CHO-K1 or HEK293 cell lines, some proportion of the expressed proteins may be sulfated at position 179, others may be sulfated at position 180, while others may be sulfated at both positions and some at neither position. This leads to a heterogeneous and unpredictable protein population with decreased potency.

The FGF21 variants of the present invention resolved this detrimental sulfation by including the amino acid substitution Y179F into the variants. Y179F eliminates the sulfation resulting from production in CHO-K1 and HEK293 cells (see Example 4). Moreover, the amino acid substitution Y179F is compatible with the other favored amino acid substitutions of the present invention, and is determined to be a neutral change with regard to potency.

Human wild type FGF21 is susceptible to proteolytic degradation in vivo. A major proteolytic fragment recovered from sera after intravenous or subcutaneous injection of mice or cynomolgus monkeys is the fragment that terminates at position 171. Previously, the FGF21 fragment spanning residues 1 to 171 has been determined to be ~100-fold less potent in in vitro potency assays. Eliminating this proteolytic cleavage site improves drug efficacy by increasing exposure to active drug. The amino acid substitution G170E has been shown to significantly slow cleavage in mouse (data not shown) and virtually eliminate proteolysis at the 171 position after 24 hours in cynomolgus monkeys (see Example 6). The G170E substitution does not impact potency and is compatible with the desired physiochemical stability profile. Therefore, the amino acid substitution G170E is incorporated into the preferred FGF21 variants of the present invention.

Human wild type FGF21 is susceptible to a carboxypeptidase produced in CHO-K1 manufacture, and the amino acid substitution S181G slows this processing, thereby reducing heterogeneity of the length of the protein expressed (i.e., heterogeneity in the number of amino acid residues in the mature protein expressed by the cell line). Although the amino acid substitution S181G does not eliminate C-terminal proteolysis in mammalian cell expression, it is quite effective at slowing proteolysis while maintaining the desired potency in the context of other desired amino acid substitutions found in the FGF21 variants of the present invention. In view of this advantageous characteristic, the amino acid substitution S181G is incorporated into the FGF21 variants of the present invention.

The present invention also encompasses polynucleotides encoding the above-described variants that may be in the form of RNA or in the form of DNA, which DNA includes cDNA and synthetic DNA. The DNA may be double-stranded or single-stranded. The coding sequences that encode the variants of the present invention may vary as a result of the redundancy or degeneracy of the genetic code.

The polynucleotides that encode for the variants of the present invention may include the following: only the coding sequence for the variants, the coding sequence for the variants and additional coding sequence such as a functional polypeptide, or a leader or secretory sequence or a pro-protein sequence; the coding sequence for the variants and non-coding sequence, such as introns or non-coding sequence 5' and/or 3' of the coding sequence for the variants. Thus the term "polynucleotide encoding a variant" encompasses a polynucleotide that may include not only coding sequence for the variants but also a polynucleotide which includes additional coding and/or non-coding sequence.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit selection of those cells transformed with the desired DNA sequences.

The FGF21 variants of the present invention may readily be produced in mammalian cells such as CHO, NS0, HEK293 or COS cells; in bacterial cells such as *E. coli, Bacillus subtilis,* or *Pseudomonas fluorescence*; or in fungal or yeast cells. The host cells are cultured using techniques well known in the art. The preferred mammalian host cell is the CHOK1SV cell line containing a glutamine synthetase (GS) expression system (see U.S. Pat. No. 5,122,464).

The vectors containing the polynucleotide sequences of interest (e.g., the variants of FGF21 and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Various methods of protein purification may be employed and such methods are known in the art and described, for example, in Deutscher, *Methods in Enzymology* 182: 83-89 (1990) and Scopes, *Protein Purification: Principles and Practice,* 3rd Edition, Springer, NY (1994).

The pharmaceutical compositions of the FGF21 variants of the present invention may be administered by any means known in the art that achieve the generally intended purpose to treat type 2 diabetes, obesity, dyslipidemia, or metabolic syndrome, or any combination thereof. The preferred route of administration is parenteral. The dosage administered will be dependent upon the age, health, and weight of the recipient, kind of concurrent treatment, if any, frequency of treatment, and the nature of the effect desired. Typical dosage levels can be optimized using standard clinical techniques and will be dependent on the mode of administration and the condition of the patient and can be determined by a person having ordinary skill in the art.

The FGF21 variants of the present invention are formulated according to known methods to prepare pharmaceutically useful compositions. A desired formulation is a stable lyophilized product that is reconstituted with an appropriate diluent or an aqueous solution of high purity with optional pharmaceutically acceptable carriers, preservatives, excipients or stabilizers [*Remington*, The Science and Practice of Pharmacy, 19th edition, Gennaro, ed., Mack Publishing Co., Easton, Pa. 1995].

The FGF21 variants of the present invention may be combined with a pharmaceutically acceptable buffer, and the pH adjusted to provide acceptable stability, and a pH acceptable for administration. Moreover, the FGF21 variants of the present invention may be placed into a container such as a vial, a cartridge, a pen delivery device, a syringe, intravenous administration tubing or an intravenous administration bag, wherein the container is a unit dose container.

The term "dyslipidemia" means a disorder of lipoprotein metabolism, including lipoprotein overproduction or deficiency. Dyslipidemia may be manifested by elevation of the total cholesterol, low-density lipoprotein (LDL) cholesterol and the triglyceride concentrations, and/or a decrease in high-density lipoprotein (HDL) cholesterol concentration in the blood.

The term "metabolic syndrome" is characterized by a group of metabolic risk factors in one person. They include: abdominal fat—in most men, a 40-inch waist or greater; high blood sugar—at least 110 milligrams per deciliter (mg/dl) after fasting; high triglycerides—at least 150 mg/dL in the bloodstream; low HDL—less than 40 mg/dl; and/or, blood pressure of 130/85 or higher.

The term "obesity" is defined as a condition in which there is an excess of subcutaneous fat in proportion to lean body mass (Stedman's Medical Dictionary 28th edition, 2006, Lippincott Williams & Wilkins).

A "patient" is a mammal, preferably a human.

The term "treating" (or "treat" or "treatment") means slowing, reducing, or reversing the progression or severity of a symptom, disorder, condition, or disease.

The term "therapeutically effective amount" refers to the amount or dose of variants of FGF21 of this invention which, upon single or multiple dose administration to a patient, provides the desired treatment.

The term "type 2 diabetes" is characterized by excess glucose production in spite of the availability of insulin, and circulating glucose levels remain excessively high as a result of inadequate glucose clearance.

The following examples may be performed essentially as described below.

EXAMPLE 1

Expression of FGF21 Variants in CHOK1SV Cells

The FGF21 variants of the present invention are produced in a mammalian cell expression system using Chinese hamster ovary (CHOK1SV) cells. Genes coding for FGF21 variants are subcloned into the glutamine synthetase (GS)-containing expression plasmid backbones (pEE12.4-based plasmids). The cDNA sequence encoding the FGF21 variants is fused in frame with the coding sequence of preferred signal peptide sequences to enhance secretion of the desired product into the tissue culture medium. The preferred signal peptide sequences are the polypeptides as shown in the amino acid sequences SEQ ID NO:3, SEQ ID NO:4, SEQ ID NO:5, or SEQ ID NO:6.

The expression is driven by the viral cytomegalovirus (CMV) promoter. CHOK1SV cells are stably transfected using electroporation and the appropriate amount of recombinant expression plasmid, and the transfected cells are maintained in suspension culture, at the adequate cell density. Selection of the transfected cells is accomplished by growth in methionine sulfoximine (MSX)-containing serum-free medium and incubated at 35-37° C. and 5-7% $CO_2$.

Clonally-derived cell lines are generated by use of a flow cytometer. The expression of an FGF21 variant in mammalian cells generally yields the natural N-terminal sequence, HPIP, i.e. without a methionine residue at the N-terminus, such as the FGF21 variant shown by the amino acid sequence of SEQ ID NO:1.

FGF21 variants secreted into the media from the CHO cells are purified by a process by which the clarified cell culture medium is heated to 50-60° C. for up to two hours, cooled, treated with detergent (Triton X-100) for viral inactivation, and is applied to a Capto MMC (GE Healthcare) mixed mode chromatography column. The FGF21 variant is eluted from the column using a pH 8 buffer, and the subsequent product pool is adjusted with 50 mM citric acid, 150 mM NaCl solution to a pH range of 3.2 to 3.5 for one hour for viral inactivation. The solution is adjusted to between pH 6.7 to 7.3 by addition of Tris buffer and the FGF21 variant is further purified by hydrophobic exchange chromatography using Phenyl Sepharose High Performance resin (GE Healthcare). The hydrophobic interaction column is eluted with a decreasing gradient of sodium sulfate at pH 7. The HIC purified FGF21 variant is buffer exchanged into a Tris buffer at pH 8 containing NaCl and is further purified by anion exchange chromatography on Source 30Q resin (GE Healthcare). The anion exchange column is eluted with an increasing concentration of sodium chloride at pH 8. Purified FGF21 variant is passed through a Planova 20N (Asahi Kasei Medical) viral retention filter followed by concentration/diafiltration into 10 mM citrate, 150 mM NaCl pH 7 using tangential flow ultrafiltration on a regenerated cellulose membrane (Millipore).

EXAMPLE 2

3T3-L1-βKlotho Fibroblast Glucose Uptake Assay

3T3-L1-βKlotho fibroblasts are generated from 3T3-L1 fibroblasts by retroviral transduction of a CMV-driven mammalian expression vector containing the coding sequence of wild type mouse βKlotho and a blasticidin resistance marker. Blasticidin-resistant cells are selected after growth for 14 days in the presence of 15 µM blasticidin, and βKlotho protein expression is verified by immunoblot with an anti-βKlotho antibody. The 3T3-L1-βKlotho fibroblasts are maintained in Dulbecco's Modified Eagle Medium (DMEM) with 10% calf serum, and 15 µM blasticidin until plated for experimental use.

For glucose uptake, 3T3-L1-βKlotho fibroblasts are plated at 20,000 cells/well in 96-well plates and incubated for 48 hours in DMEM with 10% calf serum. The cells are incubated for 3 hours in DMEM with 0.1% bovine serum albumin (BSA) with or without an FGF21 variant of interest, followed by 1 hour incubation in Krebs—Ringer phosphate (KRP) buffer (15 mM Hepes, pH 7.4, 118 mM NaCl, 4.8 mM KCl, 1.2 mM $MgSO_4$, 1.3 mM $CaCl_2$, 1.2 mM $KH_2PO_4$, 0.1% BSA) containing 100 µM 2-deoxy-D-($^{14}$C) glucose with or without an FGF21 variant. Non-specific binding is determined by incubation of select wells in Krebs—Ringer bicarbonate/Hepes (KRBH) buffer containing 1 mM 2-deoxy-D-($^{14}$C) glucose. The reaction is terminated by addition of 20 µM cytochalasin B to the cells and glucose uptake is measured using a liquid scintillation counter.

The in vitro potency of the FGF21 variant of SEQ ID NO:1 in the 3T3-L1-βKlotho fibroblast glucose uptake assay was 0.026 nM. The FGF21 variant of SEQ ID NO:1 is a potent FGF21 variant when compared to the known FGF21 variant of SEQ ID NO:11 (disclosed in WO 2006/028595). The in vitro potency of the FGF21 variant of SEQ ID NO:11 in the 3T3-L1-βKlotho fibroblast glucose uptake assay was 0.49 nM.

EXAMPLE 3

Human 293 Cell-βKlotho-SRE luciferase Assay

Construction of 293-βKlotho-SRE luc Reporter Cells:

HEK-293 (human embryonic kidney cells) are cultured at 37° C., 5% $CO_2$ in growth medium containing 10% fetal bovine serum (FBS) in Dulbecco's modified Eagle's medium. Cells are cotransfected with a plasmid containing a CMV promoter driven human βKlotho expression cassette and a plasmid containing a Serum Response Element (SRE) driven luciferase expression cassette. The βKlotho expression plasmid also contains an SV40 promoter driven neomycin phosphotransferase expression cassette to confer resistance to the aminoglycoside antibiotic G418. Transfected HEK-293 cells are selected with 600 µg/mL of G418 to select for cells where the transfected plasmids have been integrated into the genome. Selected cells are cloned by dilution and tested for an increase in luciferase production at 24 hours post addition of FGF21. The clone demonstrating the largest FGF21 dependant increase in luciferase is chosen as the cell line used to measure relative FGF21 variants activity.

293-βKlotho-SRE luc FGF21 Activity Assay:

293-βKlotho-SRE luc cells are rinsed and placed into CD 293 suspension culture media (Invitrogen). Cells are grown in suspension overnight at 37° C., 6% $CO_2$, 125 rpm. Cells are counted, pelleted by centrifugation, and re-suspended in CD 293 media containing 0.1% BSA. Cells are placed in white 96 well plates at 25,000 cells per well. A four-fold serial dilution in CD 293/0.1% BSA is prepared for each FGF21 variant to generate eight dilutions with final concentrations from 100 nM to 0.006 nM. Dilutions are added to cells in triplicate and incubated for 16-20 hours at 37° C., 5% $CO_2$. Luciferase level is determined by the addition of an equal volume of One-Glo™ luciferase substrate (Promega) and measuring relative luminescence. Data is analyzed using a four parameter logistic model (XLfit version 5.1) to fit the curves and determine $EC_{50}$.

The in vitro potency of the FGF21 variant of SEQ ID NO:1 in the human 293 cell-βKlotho-SRE luc assay was 0.25 nM. The FGF21 variant of SEQ ID NO:1 is a potent FGF21 variant when compared to the known FGF21 variant of SEQ ID NO:11 (disclosed in WO 2006/028595). The in vitro potency of the FGF21 variant of SEQ ID NO:11 in the human 293 cell-βKlotho-SRE luc assay was 22.39 nM.

EXAMPLE 4

Tyrosine Sulfation During Manufacturing in Mammalian Cells

Human wild type FGF21 is susceptible to tyrosine sulfation at position 179 during mammalian protein expression in CHOK1SV cells (data not shown). This sulfation leads to product heterogeneity, meaning that different forms of the protein (i.e., with and without sulfation) may occur. Product homogeneity is a desired attribute of a biopharmaceutical product. Post-translational modifications that occur during production of a therapeutic protein are undesirable as the modifications can lead to differences in activity or other biopharmaceutical properties.

To assess whether an FGF21 variant is sulfated, a 1 µL aliquot of the sample is mixed with 99 µL of 0.1% trifluoroacetic acid (TFA). The sample is analyzed by liquid chromatography—mass spectrometry (LC-MS), using the following conditions: the mobile phase A is 0.1% TFA/10% acetonitrile, the mobile phase B is 0.1% TFA in acetonitrile, the column is a C8 column, 3.5 µm 2.1×150 mm, with 2.1×12.5 mm C8 guard, the injection volume is 12-20 µL depending on sample concentration so that approximately 1 µg of protein is injected.

TABLE 1

Gradient Conditions for Liquid Chromatographic Separation

| | Time (min) | | | | | |
|---|---|---|---|---|---|---|
| | 0 | 12 | 15 | 15.1 | 20 | 21.1 | 30 |
| % B | 10 | 50 | 60 | 90 | 90 | 10 | 10 |
| Flow (µL/min) | 200 | 200 | 200 | 200 | 200 | 200 | 200 |

A Waters Micromass LCT Premier™ mass spectrometer is set up to a mass range between 400 to 1990 amu, polarity ES+, capillary 2000, sample cone 40 V, aperture 1 is 30 V, the source temperature is 105° C., cone gas flow is 50 L/hour, desolvation temperature is 300° C., and the desolvation gas flow is 600 L/hour.

TABLE 2

LC/MS Characterization of FGF21 variant of SEQ ID NO: 1

| Product | Expected Mass | Observed Mass | % Error | Rel % |
|---|---|---|---|---|
| 1-181 | 19633.3 | 19633.0 | 0.002 | 33.8 |
| 1-180 | 19576.2 | 19576.1 | 0.001 | 66.2 |

As can be seen from Table 2, the expected mass (having no sulfation) was approximately the same as the observed mass for the FGF21 variant of SEQ ID NO:1, indicating that sulfation was not detected in the FGF21 variant of SEQ ID NO:1. Thus, the amino acid substitution Y179F prevented sulfation from occurring at position 179 in the FGF21 variant of SEQ ID NO:1. This result provides a more homogeneous product, making it more acceptable as a therapeutic protein product.

EXAMPLE 5

P115W Promotes Aggregation, Whereas L98D Increases Physical Stability and Compatibility with Benzyl Alcohol in the Formulation To measure the amount of protein self-association and aggregation, an analytical size exclusion chromatography (SEC) method is used to measure the percent of high molecular weight (% HMW) aggregates. Initial stock solutions of protein are characterized by SEC to determine the starting levels of HMW (Table 3).

TABLE 3

| FGF21 variants | Starting Level of HMW (%) |
|---|---|
| FGF21 variant of SEQ ID NO: 10 | 3.2 |
| FGF21 variant of SEQ ID NO: 1 | 0.21 |
| FGF21 variant of SEQ ID NO: 8 | 3.6 |
| FGF21 variant of SEQ ID NO: 9 | 0.12 |

Samples of each protein are prepared by dialyzing (using dialysis cassettes with molecular weight cutoff of 10,000 daltons) into sample buffers (described in Tables 4-6) at a concentration of 2 mg/mL overnight at 4° C. After dialysis, samples are sterile filtered (0.22 μm membrane) and quantified by absorbance at 280 nm. Next, samples are concentrated to a target concentration of ≥60 mg/mL at 3000 rpm at 4° C. using 10,000 MW cut-off centrifuge filters. After concentrating samples, the protein concentration is quantified by absorbance at 280 nm, and the % HMW is determined using an SEC assay.

The SEC method utilizes a TosoHaas model TSK-GEL® $G2000SW_{XL}$ column with dimensions 30 cm×0.78 cm. Mobile phase is 0.1 M sodium phosphate, pH 7.4 at a flow rate of 0.5 mL/minute. Low concentration samples are applied as 10 μL injections and monitored at an absorbance wavelength of 214 nm, whereas concentrated samples are applied as 1 μL injections and monitored at 280 nm.

Table 4 reports protein concentration and % HMW in the concentrated solutions of the FGF21 variants SEQ ID NO:8 and SEQ ID NO:9. The percentage of each variant remaining in the monomeric (non-aggregated from) is not listed in the table but is equal to 100% minus the reported % HMW. The FGF21 variant of SEQ ID NO:8 and the FGF21 variant of SEQ ID NO:9 differ only at amino acid position 115 with the FGF21 variant of SEQ ID NO:8 containing a potency enhancing residue tryptophan at 115 (P115W) and the FGF21 variant of SEQ ID NO:9 containing the wild type residue proline (P115P). Under various formulation buffer conditions, the % HMW for the FGF21 variant of SEQ ID NO:8 (P115W) was significantly higher compared to the FGF21 variant of SEQ ID NO:9, demonstrating the causal effect of having tryptophan at position 115 on promoting aggregation and self-association. Likewise, the FGF21 variant of SEQ ID NO:10, which contains the tryptophan residue at position 115, has substantially elevated % HMW compared to the FGF21 variant of SEQ ID NO:1, which contains the amino acid proline at position 115 (Table 5).

TABLE 4

Propensity for Aggregation as Measured by SEC

| | FGF21 variant of SEQ ID NO: 8 (P115W) | | FGF21 variant of SEQ ID NO: 9 (P115P) | |
|---|---|---|---|---|
| Buffer Composition | Conc. (mg/mL) | % HMW | Conc. (mg/mL) | % HMW |
| Phosphate buffer saline pH7.4 | 65 | 32.3 | 67 | 0.38 |
| 10 mM Histidine pH7.0, 150 mM NaCl | 62 | 34.3 | 63 | 0.47 |
| 10 mM Tris pH 8.0, 150 mM NaCl | 65 | 26.5 | 64 | 0.34 |
| 10 mM Histidine pH 7.0, 150 mM NaCl, 0.2M L-arginine | 72 | 29.2 | 81 | 0.42 |
| 10 mM Histidine pH 7.0, 50 mM NaCl | 70 | 49.6 | 50 | 3.5 |

TABLE 5

Propensity for Aggregation as Measured by SEC

| | FGF21 variant of SEQ ID NO: 10 (P115W) | | FGF21 variant of SEQ ID NO: 1 (P115P) | |
|---|---|---|---|---|
| Buffer Composition | Conc. (mg/mL) | % HMW | Conc. (mg/mL) | % HMW |
| Phosphate buffer saline pH7.4 | 77 | 33.7 | 88 | 0.56 |
| 10 mM Histidine pH7.0, 150 mM NaCl | 83 | 37.5 | 61 | 0.69 |
| 10 mM Tris pH8.0, 150 mM NaCl | 63 | 25.1 | 71 | 2.4 |
| 10 mM Histidine pH7.0, 150 mM NaCl, 0.2M L-arginine | 64 | 27.8 | 85 | 2.6 |
| 10 mM Histidine pH7.0, 50 mM NaCl | 58 | 45.9 | 61 | 8.2 |

Physical stability and compatibility with benzyl alcohol at a preservative-level concentration of 0.9% is measured as % HMW in the SEC assay, monitored in the buffer 10 mM histidine at pH 7.0 with 150 mM NaCl, in the presence or absence of 0.02% Tween-80. Samples are prepared at 30 mg/mL and incubated at 4° C., 25° C., and 40° C. for 4 weeks. Freshly formulated FGF21 variants (i.e., at time zero) and those incubated for 4 weeks are analyzed for % HMW by the SEC method. Table 6 summarizes results of the analyses, comparing time zero samples ("Initial") and those incubated 4 weeks at 40° C.

TABLE 6

Propensity for Aggregation and Preservative Compatibility at 30 mg/mL Formulation Concentration

| | FGF21 variant of SEQ ID NO: 9 (L98L) | | FGF21 variant of SEQ ID NO: 1 (L98D) | |
|---|---|---|---|---|
| Buffer Composition | Initial (% HMW) | 4 weeks at 40° C. (% HMW) | Initial (% HMW) | 4 weeks at 40° C. (% HMW) |
| 10 mM Histidine, pH7.0, 150 mM NaCl | 0.97 | 18.3 | 6.0 | 5.6 |
| 10 mM Histidine, pH7.0, 150 mM NaCl, 0.9% benzyl alcohol | 11.0 | 33.9 | 4.2 | 6.0 |
| 10 mM Histidine, pH7.0, 150 mM NaCl, 0.9% benzyl alcohol, 0.02% Tween-80 | 11.0 | 32.1 | 4.3 | 5.3 |

The FGF21 variant of SEQ ID NO:1 contains the amino acid substitution L98D. The FGF21 variant of SEQ ID NO:9 does not contain the amino acid substitution L98D and instead contains the wild type amino acid leucine at position 98. The benefit of the amino acid substitution L98D is observed when each protein is formulated at 30 mg/mL under formulation conditions (Table 6). Under all conditions tested, stressing the FGF21 variants for 4 weeks at 40° C. results in a substantially higher % HMW for the FGF21 variant of SEQ ID NO:9 compared to the FGF21 variant of SEQ ID NO:1. Furthermore, addition of 0.9% benzyl alcohol, a common preservative used in a multi-use pharmaceutical preparation, exacerbates the increase in % HMW for the FGF21 variant of SEQ ID NO:9 but not for the FGF21 variant of SEQ ID NO:1. This incompatibility with benzyl alcohol is also observed in the analysis of the initial sample preparation, where the %

HMW in the presence of 0.9% benzyl alcohol is 11%, compared to only 0.97% in the absence of benzyl alcohol. Neither the FGF21 variant of SEQ ID NO:9 nor the FGF21 variant of SEQ ID NO:1 contain the P115W residue, thus, the poor physical stability under these conditions cannot be attributed to the P115W residue. After the amino acid substitution L98D is made, enhanced physical stability in the presence of 0.9% benzyl alcohol is observed.

These data indicate that certain substitutions can affect the stability of overall protein due to aggregation into high molecular weight species, particularly in the presence of certain preservatives such as benzyl alcohol. Minimization of these HMW aggregates is preferred for therapeutic proteins. This can be accomplished through certain substitutions in the FGF21 variants protein, such as L98D in the FGF21 variants shown in SEQ ID NO:1. Other substitutions, such as P115W, can have detrimental effects, such as increasing the level of aggregation in the variants.

EXAMPLE 6

Proteolytic Degradation In Vivo

Male cynomolgus monkeys, n=2/group are dosed subcutaneously with a single 2 mg/kg injection of the FGF21 variant of SEQ ID NO:1. Serum is obtained over the time course (withdrawn after 0.25 to 12 hours) for 24 hour evaluation of in vivo proteolysis via mass spectrometry to quantify the amount of active compound.

Liquid chromatographic mass spectrometry (LC/MS) analysis is performed. A 100 μL aliquot of each serum sample is immunoprecipitated with anti-FGF21 monoclonal antibodies which are covalently bound to magnetic beads. The immunoprecipitated samples are split into separate aliquots, allowing detection of intact proteins and tryptically-digested proteins. Intact proteins are injected onto a Discovery® Bio wide pore column, 100×0.32 mm i.d. containing 3 μm particles coated with C5. Tryptically-digested samples are injected onto a Discovery Biowide Pore column, 100×0.32 mm i.d. containing 3 μm particles coated with C18. Chromatographic conditions for all injections use binary gradients consisting of mobile phase A (0.1/100, formic acid:water) and mobile phase B (0.1/100, formic acid:acetonitrile). The effluent from the LC is directly connected to a Micromass Synapt® Q-Tof mass spectrometer for mass spectral detection in positive ion mode. Data from the Q-Tof mass spectrometer are collected using Masslynx (v 4.1) and MaxEnt1 deconvolution software.

Cleavage at position 171 of FGF21 proteins has been found to reduce bioactivity of the protein by over 100-fold. Thus, reducing the proteolysis at this site is desirable to enhance exposure of fully-active drug. The FGF21 variant of SEQ ID NO:1, when analyzed in an LC/MS method as above, shows no detectable proteolysis products over the 24 hour evaluation. These data demonstrate the substitution of G170E in the FGF21 variant of SEQ ID NO:1 diminishes in vivo proteolytic degradation over 24 hours in male cynomolgus monkeys when compared to the FGF21 variant of SEQ ID NO:7, which does not contain the amino acid substitution of G170E.

EXAMPLE 7

Glucose Lowering in Ob/Ob Mouse Model

Male ob/ob (B6.V-Lep$^{ob}$/Lep$^+$/OlaHsd) mice and age-matched ob/m lean controls (B6.V-Lep$^+$/OlaHsd) are 7-8 weeks of age upon arrival and 10-11 weeks of age at initiation of treatment. Upon arrival, all mice are housed 3 per cage and allowed to acclimate for 3 weeks before the start of treatment. The mice are fed Purina Rodent Chow 5015 and given water ad libitum. The mice are housed in 12-hour light/dark cycle with ambient temperature set at 70° F. The day prior to initiation of treatment, the mice are fasted for 2 hours and blood samples are collected via tail bleed into heparinized capillary tubes. Blood glucose levels are measured with an Ascensia Contour blood glucose meter and plasma insulin levels are quantified using the Meso Scale mouse/rat insulin assay kit (Meso Scale Discovery, Gaithersburg, Md.). On the day of treatment initiation (day 0), the mice are sorted based on previous day's body weight, blood glucose, and plasma insulin. The FGF21 variants are diluted with sterile saline (0.9% NaCl) and administered subcutaneously via mini-osmotic Alzet pumps. On day 5, fed blood glucose and plasma insulin levels are measured approximately 2 hours after the start of the light cycle. All mice are fasted overnight on day 5 and an oral glucose tolerance test (OGTT) is performed on day 6. The mice are bled via tail snip into heparinized capillary tubes prior to oral administration of glucose (2 g/kg). Additional blood samples are collected 30, 60, and 120 minutes after oral glucose administration. Plasma glucose is measured with a glucose assay kit from Cayman Chemicals. A four parameter logistic regression model fit is performed on the normalized glucose AUC values on day 6.

On day 5, vehicle-treated mice were hyperglycemic with mean blood glucose levels measured at 240.4±15.0 mg/dl (mean±SEM), while ob/m lean control mice had blood glucose levels of 150.6±6.0 mg/dl (mean±SEM). Both the FGF21 variant of SEQ ID NO:1 and the FGF21 variant of SEQ ID NO:11 lowered blood glucose in a dose-dependent manner to levels comparable to the ob/m lean controls. The $ED_{50}$ of the FGF21 variant of SEQ ID NO:1 was 0.7 μg/kg/hr, while the $ED_{50}$ of the FGF21 variant of SEQ ID NO:11 was 3.1 μg/kg/hr. The FGF21 variant of SEQ ID NO:1 was approximately 4.4-fold more potent at lowering blood glucose in ob/ob mice than the FGF21 variant of SEQ ID NO:11. Therefore, the FGF21 variant of SEQ ID NO:1 is a potent FGF21 variant when compared to the known FGF21 variant of SEQ ID NO:11 (disclosed in WO 2006/028595).

We claim:

1. A variant of human fibroblast growth factor 21 (FGF21), wherein the amino acid sequence is (SEQ ID NO: 13)
HPIPDSSPLLQFGGQVRQRYLYTDDAQQTECHLEIREDGTVGCAADQS

PESLLQLKALKPGVIQILGVKTSRFLCQRPDGALYGSLHFDPEACSFR

E$X_1$LLEDGYNVYQSEAHGL$X_2$LHLPGDKSPHRKPAPRGPARFLPLPGLP

PALPEPPGILAPQPPDVGSSDP$X_3 X_4$LV$X_5$PSQLLSPSFLG wherein $X_1$ is L or D, $X_2$ is P or W, $X_3$ is L or Y, $X_4$ is S or R, and $X_5$ is G or E.

2. The variant of claim 1, wherein X1 is D, X2 is P, and X5 is E.

3. A method for treating type 2 diabetes, obesity, dyslipidemia, or metabolic syndrome, or any combination thereof, comprising administering the variant of claim 1 to a patient in need thereof.

4. A method for treating type 2 diabetes, obesity, dyslipidemia, or metabolic syndrome, or any combination thereof, comprising administering the variant of claim 2 to a patient in need thereof.

5. A pharmaceutical composition comprising the variant of claim 1, and at least one pharmaceutically acceptable carrier, diluent, or excipient.

6. A pharmaceutical composition comprising the variant of claim 2, and at least one pharmaceutically acceptable carrier, diluent, or excipient.

* * * * *

SEQUENCE LISTING

<160> NUMBER OF SEQ ID NOS: 13

<210> SEQ ID NO 1
<211> LENGTH: 181
<212> TYPE: PRT
<213> ORGANISM: Artificial Sequence
<220> FEATURE:
<223> OTHER INFORMATION: Synthetic Construct

<400> SEQUENCE: 1

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Asp Leu Leu Glu Asp Gly Tyr Asn Val Tyr Gln Ser Glu Ala His
            100                 105                 110

Gly Leu Pro Leu His Leu Pro Gly Asp Lys Ser Pro His Arg Lys Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Arg Leu Val Glu Pro Ser Gln Leu Leu Ser
                165                 170                 175

Pro Ser Phe Leu Gly
            180

<210> SEQ ID NO 2
<211> LENGTH: 181
<212> TYPE: PRT
<213> ORGANISM: Homo sapiens

<400> SEQUENCE: 2

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
```

180

<210> SEQ ID NO 3
<211> LENGTH: 19
<212> TYPE: PRT
<213> ORGANISM: Artificial Sequence
<220> FEATURE:
<223> OTHER INFORMATION: Synthetic Construct

<400> SEQUENCE: 3

```
Met Arg Leu Ala Val Gly Ala Leu Leu Val Cys Ala Val Leu Gly Leu
1               5                   10                  15

Cys Leu Ala
```

<210> SEQ ID NO 4
<211> LENGTH: 23
<212> TYPE: PRT
<213> ORGANISM: Artificial Sequence
<220> FEATURE:
<223> OTHER INFORMATION: Synthetic Construct

<400> SEQUENCE: 4

```
Met Lys Ile Cys Ser Leu Thr Leu Leu Ser Phe Leu Leu Leu Ala Ala
1               5                   10                  15

Gln Val Leu Leu Val Glu Gly
            20
```

<210> SEQ ID NO 5
<211> LENGTH: 18
<212> TYPE: PRT
<213> ORGANISM: Artificial Sequence
<220> FEATURE:
<223> OTHER INFORMATION: Synthetic Construct

<400> SEQUENCE: 5

```
Met Lys Ala Leu Val Ile Leu Gly Phe Leu Phe Leu Ser Val Ala Val
1               5                   10                  15

Gln Gly
```

<210> SEQ ID NO 6
<211> LENGTH: 20
<212> TYPE: PRT
<213> ORGANISM: Artificial Sequence
<220> FEATURE:
<223> OTHER INFORMATION: Synthetic Construct

<400> SEQUENCE: 6

```
Met Glu Thr Asp Thr Leu Leu Leu Trp Val Leu Leu Leu Trp Val Pro
1               5                   10                  15

Gly Ser Thr Gly
            20
```

<210> SEQ ID NO 7
<211> LENGTH: 181
<212> TYPE: PRT
<213> ORGANISM: Artificial Sequence
<220> FEATURE:
<223> OTHER INFORMATION: Synthetic Construct

<400> SEQUENCE: 7

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
                20                  25                  30
```

Leu Glu Ile Arg Glu Asp Gly Thr Val Gly Cys Ala Ala Asp Gln Ser
            35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Asp Leu Leu Glu Asp Gly Tyr Asn Val Tyr Gln Ser Glu Ala His
            100                 105                 110

Gly Leu Pro Leu His Leu Pro Gly Asp Lys Ser Pro His Arg Lys Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Asp Val
145                 150                 155                 160

Gly Ser Ser Asp Pro Leu Arg Leu Val Gly Pro Ser Gln Leu Leu Ser
                165                 170                 175

Pro Ser Phe Leu Gly
            180

<210> SEQ ID NO 8
<211> LENGTH: 181
<212> TYPE: PRT
<213> ORGANISM: Artificial Sequence
<220> FEATURE:
<223> OTHER INFORMATION: Synthetic Construct

<400> SEQUENCE: 8

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
            35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Trp Leu His Leu Pro Gly Asp Lys Ser Pro His Arg Lys Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Asp Val
145                 150                 155                 160

Gly Ser Ser Asp Pro Tyr Ser Leu Val Glu Pro Ser Gln Leu Leu Ser
                165                 170                 175

Pro Ser Phe Leu Gly
            180

<210> SEQ ID NO 9

```
<211> LENGTH: 181
<212> TYPE: PRT
<213> ORGANISM: Artificial Sequence
<220> FEATURE:
<223> OTHER INFORMATION: Synthetic Construct

<400> SEQUENCE: 9

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asp Lys Ser Pro His Arg Lys Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Tyr Ser Leu Val Glu Pro Ser Gln Leu Leu Ser
                165                 170                 175

Pro Ser Phe Leu Gly
            180

<210> SEQ ID NO 10
<211> LENGTH: 181
<212> TYPE: PRT
<213> ORGANISM: Artificial Sequence
<220> FEATURE:
<223> OTHER INFORMATION: Synthetic Construct

<400> SEQUENCE: 10

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Trp Leu His Leu Pro Gly Asp Lys Ser Pro His Arg Lys Pro
        115                 120                 125

Ala Pro Arg Gly Pro Ala Arg Phe Leu Pro Leu Pro Gly Leu Pro Pro
```

Ala Leu Pro Glu Pro Pro Gly Ile Leu Ala Pro Gln Pro Pro Asp Val
145                 150                 155                 160

Gly Ser Ser Asp Pro Leu Arg Leu Val Glu Pro Ser Gln Leu Leu Ser
            165                 170                 175

Pro Ser Phe Leu Gly
            180

<210> SEQ ID NO 11
<211> LENGTH: 177
<212> TYPE: PRT
<213> ORGANISM: Artificial Sequence
<220> FEATURE:
<223> OTHER INFORMATION: Synthetic Construct

<400> SEQUENCE: 11

Asp Ser Ser Pro Leu Leu Gln Phe Gly Gly Gln Val Arg Gln Arg Tyr
1               5                   10                  15

Leu Tyr Thr Asp Asp Ala Gln Gln Thr Glu Ala His Leu Glu Ile Arg
            20                  25                  30

Glu Asp Gly Thr Val Gly Gly Ala Ala Asp Gln Ser Pro Glu Ser Leu
        35                  40                  45

Leu Gln Leu Lys Ala Leu Lys Pro Gly Val Ile Gln Ile Leu Gly Val
    50                  55                  60

Lys Thr Ser Arg Phe Leu Cys Gln Arg Pro Asp Gly Ala Leu Tyr Gly
65                  70                  75                  80

Ser Leu His Phe Asp Pro Glu Ala Cys Ser Phe Arg Glu Leu Leu Leu
                85                  90                  95

Glu Asp Gly Tyr Asn Val Tyr Gln Ser Glu Ala His Gly Leu Pro Leu
            100                 105                 110

His Cys Pro Gly Asn Lys Ser Pro His Arg Asp Pro Ala Pro Arg Gly
        115                 120                 125

Pro Cys Arg Phe Leu Pro Leu Pro Gly Leu Pro Pro Ala Leu Pro Glu
    130                 135                 140

Pro Pro Gly Ile Leu Ala Pro Gln Pro Pro Asp Val Gly Ser Ser Asp
145                 150                 155                 160

Pro Leu Ala Met Val Gly Pro Ser Gln Gly Arg Ser Pro Ser Tyr Ala
                165                 170                 175

Ser

<210> SEQ ID NO 12
<211> LENGTH: 543
<212> TYPE: DNA
<213> ORGANISM: Artificial Sequence
<220> FEATURE:
<223> OTHER INFORMATION: Synthetic Construct

<400> SEQUENCE: 12 cacccctatcc ctgactccag ccctctgctg cagtttggcg acaggtccg gcagcggtac      60 ctgtacaccg acgacgccca gcagaccgag tgccacctgg aaatccggga ggacggcacc    120
gtgggctgtg ccgccgacca gtcccctgag tccctgctgc agctgaaggc cctgaagcct    180
ggcgtgatcc agatcctggg cgtgaaaacc tcccggttcc tgtgccagag gcctgatggc    240 gcccctgtacg gctccctgca cttcgaccct gaggcctgct ccttccggga ggacctgctg    300
gaagatggct acaacgtgta ccagtccgag gctcacggcc tgcctctgca tctgcctggc    360
gacaagtccc cccaccggaa gcctgctcct agggggccctg ccagattcct gccactgcct    420

```
ggcctgcctc cagctctgcc tgagcctcct ggcatcctgg ccccteagee tecagacgtg      480 ggctcctccg accctctgcg gctggtcgag ccttcccagc tgctgagccc tagcttcctg      540
ggc                                                                   543
```

```
<210> SEQ ID NO 13
<211> LENGTH: 181
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (98)..(98)
<223> OTHER INFORMATION: Xaa at position 98 is Leu or Asp
<220> FEATURE:
<221> NAME/KEY: MISC_FEATURE
<222> LOCATION: (115)..(115)
<223> OTHER INFORMATION: Xaa at position 115 is Pro or Trp
<220> FEATURE:
<221> NAME/KEY: MISC_FEATURE
<222> LOCATION: (166)..(166)
<223> OTHER INFORMATION: Xaa at position 166 is Leu or Tyr
<220> FEATURE:
<221> NAME/KEY: MISC_FEATURE
<222> LOCATION: (167)..(167)
<223> OTHER INFORMATION: Xaa at position 167 is Ser or Arg
<220> FEATURE:
<221> NAME/KEY: MISC_FEATURE
<222> LOCATION: (170)..(170)
<223> OTHER INFORMATION: Xaa at position 170 is Gly or Glu

<400> SEQUENCE: 13

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Xaa Leu Leu Glu Asp Gly Tyr Asn Val Tyr Gln Ser Glu Ala His
            100                 105                 110

Gly Leu Xaa Leu His Leu Pro Gly Asp Lys Ser Pro His Arg Lys Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Xaa Xaa Leu Val Xaa Pro Ser Gln Leu Leu Ser
                165                 170                 175

Pro Ser Phe Leu Gly
            180
```